United States Patent [19]

Lupichuk

[11] 4,070,404

[45] Jan. 24, 1978

[54] PROCESS TO 1,1-DIHALO-4-METHYL-1,3-PENTADIENES, PYRETHROID INSECTICIDE INTERMEDIATES

[75] Inventor: Andrew Lupichuk, Hamilton Square, N.J.

[73] Assignee: FMC Corporation, Philadelphia, Pa.

[21] Appl. No.: 670,791

[22] Filed: Mar. 26, 1976

[51] Int. Cl.$^2$ ............................................. C07C 21/00
[52] U.S. Cl. ................................. 260/654 D; 260/633; 260/658 C; 560/124
[58] Field of Search .......... 260/468 H, 654 D, 654 R, 260/655

[56] References Cited

U.S. PATENT DOCUMENTS

| | | | |
|---|---|---|---|
| 2,410,541 | 11/1946 | Joyce | 260/654 D |
| 2,561,516 | 7/1951 | Ladd | 260/487 |
| 2,613,221 | 10/1952 | Ladd | 260/493 |
| 2,725,411 | 11/1955 | Ladd | 260/655 |
| 3,471,579 | 10/1969 | Kubicek | 260/633 |
| 3,862,978 | 1/1975 | Decker | 260/487 |
| 4,018,838 | 4/1977 | Cleare | 260/654 D |

FOREIGN PATENT DOCUMENTS 73-3528  5/1973  South Africa.

OTHER PUBLICATIONS

Elliot, et al., Nature, 244, 456 (1973).
Elliot, et al., Nature, 246, 169 (1973).
Farkas, et al., Coll. Czech. Chem. Comm., 24, 2230 (1959).
Kharasch, et al., J. Amer. Chem. Soc., 69, 1100 (1947).
Kharasch, et al., J. Amer. Chem. Soc., 69, 1105 (1947).
Reeve, et al., Can. J. Chem., 41, 2231 (1963).
Saunders, Chem. & Eng. News, p. 19 (7/28/75).
Saunders, Acc. Chem. Res., 9, 19 (1976).

*Primary Examiner*—Robert Gerstl
*Assistant Examiner*—Michael Shippen
*Attorney, Agent, or Firm*—Richard L. Hansen; Henry R. Ertelt

[57] ABSTRACT

1,1-Dihalo-4-methyl-1,3-pentadienes, key intermediates in the synthesis of insecticidal dihalovinylcyclopropanecarboxylates, result from the condensation of 3-methyl-1-butene with a carbon tetrahalide in the presence of a catalyst, followed by the base-induced dehydrohalogenation of the 1,1,1,3-tetrahalo-4-methylpentane resulting from the condensation.

12 Claims, No Drawings

PROCESS TO 1,1-DIHALO-4-METHYL-1,3-PENTADIENES, PYRETHROID INSECTICIDE INTERMEDIATES

BACKGROUND OF THE INVENTION

1. Field of the Invention

This invention relates to a new and improved chemical process for preparing a 1,1-dihalo-4-methyl-1,3-pentadiene, an intermediate in a known method for the production of certain pyrethroid insecticides.

2. Description of the Prior Art

Pyrethroids, naturally-occurring and synthetic derivatives of cyclopropanecarboxylic acid, have long been of interest as insecticides because they are active against a wide range of insect species, they display relatively low toxicity toward mammals, and they do not leave harmful residues. A notable recent technical advance in the pyrethroid art was the discovery of a dihalovinylcyclopropanecarboxylate, 3-phenoxybenzyl 2-($\beta,\beta$-dichlorovinyl)-3,3-dimethylcyclopropanecarboxylate, having an outstanding combination of insecticidal properties [Elliott et al., Nature, 244, 456 (1973); ibid., 246 169 (1973); South African 73/3528]. Since Elliott's discovery, a great deal of interest has been generated worldwide in economical processes for the production of this type of pyrethroid.

Several years before Elliott's discovery, a method for the production of ethyl 2-($\beta,\beta$-dichlorovinyl)-3,3-dimethylcyclopropanecarboxylate was reported [Farkas et al., Coll. Czech. Chem. Comm., 24, 2230 (1959)]. This compound leads to the Elliott pyrethroid by ester interchange [Nature, 244, 456 (1973)]. According to the Farkas method, chloral may be condensed with either isobutenyl magnesium bromide or with isobutylene, using a free radical catalyst with the latter, to produce a mixture of pentenols, which then may be reacted as follows:

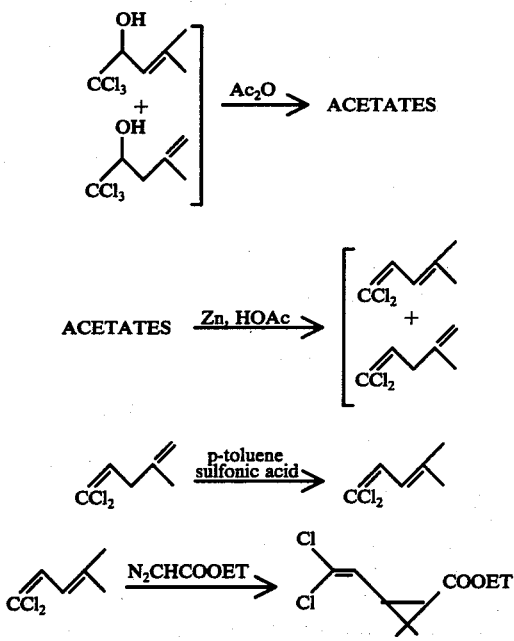

By this method the overall conversion of isobutylene to 1,1-dichloro-4-methyl-1,3-pentadiene, the key intermediate for the diazotization step, is reportedly less than 40%. Furthermore, for every kilogram of 1,1-dichloro-4-methyl-1,3-pentadiene produced, more than a kilogram of zinc dust is consumed. In a recent year, U.S. producers alone sold about 300 million kilograms of synthetic organic insecticides [Chemical and Engineering News, July 28, 1975, p. 19]. If the Elliott pyrethroid becomes a major agricultural commodity, commercial production of 1,1-dichloro-4-methyl-1,3-pentadiene by the Farkas method would seriously tax the world supply of zinc. Thus, other more practical and economical processes capable of yielding 1,1-dichloro-4-methyl-1,3-pentadiene from readily available starting materials have been sought.

As Farkas recognized, dienes of the type represented by 1,1-dichloro-4-methyl-1,3-pentadiene generally are prepared by the alkaline or pyrolytic dehydrohalogenation of 1,1,1,3-tetrachloroalkanes, which, in turn, are produced by the condensation of an alkene with carbon tetrachloride in the presence of a free radical catalyst [M. S. Kharasch et al., J. Amer. Chem. Soc., 69, 1100 (1947); ibid., 69, 1105 (1947)].

Following the general methods, Farkas attempted to make 1,1-dichloro-4-methyl-1,3-pentadiene by the dehydrohalogenation of 1,1,1,3-tetrachloro-4-methylpentane, but his efforts along this line were completely unsuccessful. Although the condensation between carbon tetrachloride and 3-methyl-1-butene proceeded in 38% yield, the treatment of 1,1,1,3-tetrachloro-4-methylpentane with base failed to produce a detectable amount of the desired 1,1,-dichloro-4-methyl-1,3-pentadiene. Furthermore, pyrolytic dehydrohalogenation of 1,1,1,3-tetrachloro-4-methylpentane "led only to dark colored tars" [Coll. Czech. Chem. Comm., 24, 2230 (1959)].

Thus, Farkas was compelled to adopt the costly, commercially unattractive method diagrammed above for the synthesis of the 1,1-dichloro-4-methyl-1,3-pentadiene required to produce the cyclopropanecarboxylate.

SUMMARY OF THE INVENTION

It has now been discovered that, contrary to and in spite of the teachings of the prior art just cited, 1,1-dichloro-4-methyl-1,3-pentadiene can be prepared in good yield from 3-methyl-1-butene and a carbon tetrahalide, via a 1,1,1,3-tetrahalo-4-methylpentane, by dehydrohalogenating the latter with base.

According to the process of this invention, 3-methyl-1-butene is condensed with a carbon tetrahalide, $CX_4$, in the presence of a catalyst to produce a 1,1,1,3-tetrahalo-4-methylpentane. The 1,1,1,3-tetrahalo-4-methylpentane is then treated with a base to produce either the desired 1,1-dihalo-4-methyl-1,3-pentadiene, resulting from the elimination of two moles of hydrohalic acid, or an intermediate olefin, representing the elimination of one mole of acid, which may then be carried to the 1,1-dihalo-4-methyl-1,3-pentadiene in further processing steps. This invention will be clarified by reference to the following chemical equations which illustrate it and by the detailed description which follows the equations.

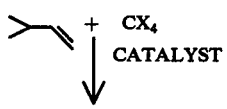

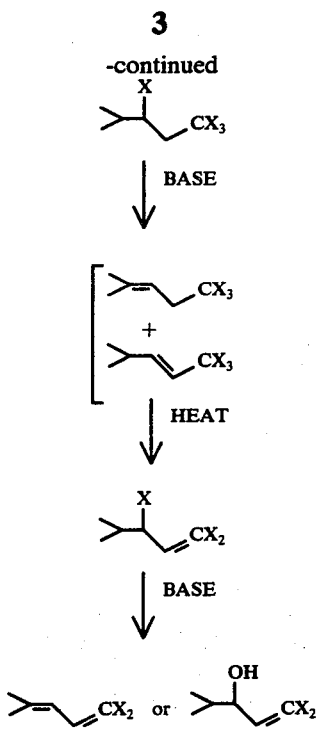

DETAILED DESCRIPTION OF THE INVENTION

In the first step of the process of this invention 3-methyl-1-butene is condensed with a carbon tetrahalide in the presence of a catalyst to produce a 1,1,1,3-tetrahalo-4-methylpentane. In order to produce a 1,1-dichloro derivative, the carbon tetrahalide will be selected from the group consisting of carbon tetrachloride, bromotrichloromethane and dibromodichloromethane. The reaction may be carried out in a solvent, and the aforesaid carbon tetrahalides may serve as both solvents and reactants. the ratio of carbon tetrahalide to 3-methyl-1-butene may lie in the range of about 1-6 on a mole to mole basis, but approximately a threefold molar excess of the carbon tetrahalide is preferred. Largely because of its low cost and availability, carbon tetrachloride generally is employed.

A catalyst is required in the reaction, and a number of such catalysts are known to those skilled in the art. These catalysts include, for example, peroxides such as benzoyl peroxide, t-butylperoxyacetate, and t-butylperoxymaleic acid; azobisisobutyronitrile; and coordination complexes such as the butylamine-ferric chloride hexahydrate complex. Of these catalysts, benzoyl peroxide generally is preferred because of its availability. The molar ratio of carbon tetrahalide to catalyst can vary between about 35/1 and 1000/1, but the best yields are obtained when the ratio is about 50/1. In order to ensure the highest possible yield, it is desirable to add the catalyst in more than one portion. It has been found that yields as high as 80% can be obtained when benzoyl peroxide is used as the catalyst and the reaction is conducted in a vitreous-line autoclave.

The condensation should be conducted under an inert atmosphere, such as nitrogen or argon for example, at a temperature in the range of about 80° C. to 110° C., preferably at about 90°-95° C. The reaction will take place at atmospheric pressure, but it may also be conducted in an autoclave under pressure. The 1,1,1,3-tetrahalo-4-methylpentane produced thereby can be separated conveniently by fractional distillation.

The preparation of 1,1,1,3-tetrahalo-4-methylpentanes is illustrated more completely by reference to Example I. In the Examples which follow, unless stated otherwise, temperatures are in degrees centigrade, and pressures are in mm of mercury. Where ir spectra are given, only the frequencies of the most prominent absorption maxima appear. Tetramethylsilane was employed as an internal standard for the nmr spectra. In reporting the nmr data, the abbreviations have the following significance: s, singlet; d, doublet; t, triplet; q, quartet; m, multiplet. Any of these abbreviations may be preceded by b for broad or d for double, for example, dd, double doublet, bt, broad triplet. Vapor phase chromatographic analyses were performed by employing a 1.2 m × 0.32 cm column packed with a silicone suspended in diatomaceous earth. The injection port temperature was 275°. The helium flow rate was 30 ml/min. The initial column temperature was 90°. The instrument was programmed to increase the column temperature at the rate of 10°/min to 250°. The thermal conductivity temperature was 275°.

EXAMPLE I

Synthesis of 1,1,1,3-Tetrahalo-4-methylpentanes

A. Synthesis of 1,1,1,3-Tetrachloro-4-methylpentane

1. Using benzoyl peroxide

A mixture of 3506 grams (22.79 moles) of carbon tetrachloride and 63 grams (0.260 mole) of benzoyl peroxide was charged into a 3.8 liter vitreous-lined autoclave. The autoclave was closed and flushed twice with nitrogen. To the stirred mixture was added 275 grams (3.92 moles) of 3-methyl-1-butene. The reaction mixture was then heated at 90°-93° for 18 hours, during which the pressure varied between 3.4 and 4.4 Kg/cm². After being cooled to 8°, the autoclave was opened. To the reaction mixture was then added an additional 31.5 grams (0.130 mole) of benzoyl peroxide. The autoclave was closed and flushed with nitrogen. Heating at 90°-93°, 2.7-3.4 Kg/cm², was resumed for 5 hours. Then the reaction mixture was distilled under vacuum to give 711 grams (80.8% yield) of 1,1,1,3-tetrachloro-4-methylpentane; bp, 97°-100°/22mm.

2. Using t-butylperoxyacetate

A pressure bottle was charged with 59.0 grams (0.384 mole) of carbon tetrachloride. The bottle and its contents were cooled to between 0° and 5°, and 4.5 grams (0.064 mole) of 3-methyl-1-butene and 0.8 gram of t-butylperoxyacetate were added. The bottle was sealed, and the stirred mixture was heated on a steambath (90°-95°) for 20 hours. The unreacted carbon tetrachloride was removed under reduced pressure, leaving 10.7 grams (76% yield) of oil. Gas chromatographic analysis of the oil indicated it to be 1,1,1,3-tetrachloro-4-methylpentane.

3. Using t-butylperoxymaleic acid

By the procedure of Example I A.2., but substituting 0.7 gram of t-butylperoxymaleic acid as the catalyst, there was obtained 6.1 grams of an oil, identified as 1,1,1,3-tetrachloro-4-methylpentane.

4. Using azobisisobutyronitrile

By the procedure of Example I A.2., but using 29.5 grams (0.192 mole) of carbon tetrachloride, and substituting 0.04 gram of azobisisobutyronitrile as the catalyst, there was obtained 3.0 grams of an oil, analyzed to contain predominantly 1,1,1,3-tetrachloro-4-methylpentane.

B. Synthesis of 3-Bromo-1,1,1-trichloro-4-methylpentane

A mixture of 595.2 grams (3.00 moles) of bromotrichloromethane and 8.3 grams (0.034 mole) of benzoyl peroxide was charged into a one liter vitreous-lined autoclave. The autoclave was closed and flushed twice with nitrogen. To the stirred mixture was added 70 grams (0.998 mole) of 3-methyl-1-butene. The reaction mixture was heated at 92°–110° for 18 hours, during which the pressure varied between 7.0 and 7.7 Kg/cm². After cooling to 10°, the autoclave was opened. An additional 8.3 grams (0.034 mole) of benzoyl peroxide was added to the reaction mixture. The reaction mixture was heated a 92°–95° and atmospheric pressure for 5 hours, and then distilled under vacuum to give 156 grams (58% yield) of 3-bromo-1,1,1-trichloro-4-methylpentane; bp, 83°–90°/7–10 mm.

The second step in the process of this invention is the base-induced dehydrohalogenation of the 1,1,1,3-tetrahalo-4-methylpentane produced in the first step.

It is well known that beta eliminations, represented by the dehydrohalogenation of a 1,1,1,3-tetrahalo-4-methylpentane, seldom occur cleanly. Mechanistically, the base-induced beta elimination of hydrohalic acid from an alkyl halide is thought to be a concerted process, wherein the alkyl halide reacts with a nucleophilic species (the base, the solvent, or the conjugate base of the solvent) in the rate-determining step [Saunders, *Acc. Chem. Res.*, 9, 19 (1976)]. This mechanism is very similar to the familiar $SN_2$ mechanism for nucleophilic aliphatic substitution. Thus, when an alkyl halide is reacted with a nucleophilic species, a mixture of products representing both substitution and elimination typically results. For example, Farkas and coworkers [*Coll. Czech. Chem. Comm.*, 24, 2230 (1959)] reported that when 1,1,1,3-tetrachloro-4-methylpentane was treated with 2 equivalents of potassium hydroxide in ethanol at 20°, the product consisted of a mixture of 1,1-dichloro-3-ethoxy-4-methyl-1-pentene (representing elimination of one chlorine atom and substitution of another), and either 1,1,1-trichloro-4-methyl-2-pentene or 1,1,3-trichloro-4-methyl-1-pentene (representing elimination). Any ether, such as 1,1-dichloro-3-ethoxy-4-methyl-1-pentene, resulting from a competing sustitution reaction will detract from the yield of 1,1-dihalo-4-methyl-1,3-pentadiene which ultimately can be produced from a 1,1,1,3-tetrahalo-4-methylpentane by dehydrohalogenation.

Not every substitution reaction occurring during the treatment of a 1,1,1,3-tetrahalo-4-methylpentane with base is wasteful, however. Thus, for example, if a 1,1-dihalo-3-hydroxy-4-methyl-1-pentene is produced, rather than the 3-alkoxy compound, dehydration of the former can lead to the desired 1,1-dihalo-4-methyl-1,3-pentadiene.

It has now been discovered that the dehydrohalogenation of a 1,1,1,3-tetrahalo-4-methylpentane can be effected under a variety of conditions, yielding either the desired 1,1-dihalo-4-methyl-1,3-pentadiene directly, or an intermediate olefin, which may be carried to the diene in further processing steps. The nature of the product of the dehydrohalogenation reaction is primarily a function of the temperature and the solvent, if a solvent is employed.

If the reaction is conducted at a low temperature, about 0°, one mole of hydrohalic acid is eliminated, and olefins are produced, without regard to the nature of the solvent. At higher temperatures, rearrangement and/or substitution may also occur, but all of these reactions can be utilized, as set forth herein, to produce the desired 1,1-dihalo-4-methyl-1,3-pentadiene.

A 1,1-dihalo-4-methyl-1,3-pentadiene may be obtained directly from a 1,1,1,3-tetrahalo-4-methylpentane by treating the latter with a base in a solvent of low nucleophilicity. Such solvents include, for example, hydrocarbons as n-hexane, n-heptane, benzene, toluene, xylene, and tetralin; ethers such as tetrahydrofuran and dioxane; as well as acetonitrile, dimethylsulfoxide and pyridine.

Various bases may be utilized, including sodium carbonate and amines such as, for example, 2,4,6-trimethylpyridine. However, strong bases such as the alkali metal hydroxides give higher yields, and are preferred. Since the reaction mixture is heterogeneous, it is preferable that a solid base, such as potassium hydroxide, be reduced to a fine powder to increase the surface area, and that vigorous stirring be employed. In order for the elimination of two moles of hydrohalic acid to occur, it is necessary to employ two equivalents of base per mole of 1,1,1,3-tetrahalo-4-methylpentane, but excess base may be used, ranging to about 10 equivalents of base per mole of 1,1,1,3-tetrahalo-4-methylpentane.

The reaction can be carried out effectively at temperatures ranging from about 100° to about 150°. At lower temperatures the elimination of the second mole of hydrohalic acid tends to be incomplete within reasonable reaction times.

The reaction time will vary of course, depending upon the nature of the solvent, the base, and the temperature. For example, when potassium hydroxide is used, and the reaction is conducted at about 100° in n-heptane, a reaction time of 5–6 hours gives the product in good yield. Continued heating leads to the formation of byproducts at the expense of the desired material.

At the completion of the reaction, the 1,1-dihalo-4-methyl-1,3-pentadiene may be separated from the solvent and other reactants by fractional distillation. Example II further illustrates this variant of the process.

The dehydrohalogenation of a 1,1,1,3-tetrahalo-4-methylpentane to a 1,1-dihalo-4-methyl-1,3-penadiene can also be conducted successfully in solvents of higher nucleophilicity, provided that only the first mole of hydrohalic acid is eliminated therein. Such solvents include alcohols; for example, methanol, ethanol, isopropanol, isobutanol, and t-butanol; as well as water.

The bases described above as being effective in solvents of low nucleophilicity may also be employed when the solvents just named are utilized. Where only one mole of hydrohalic acid is to be eliminated, only one equivalent of base is required. However, excess base is not detrimental so long as the temperature is not allowed to rise above about 0°. If the temperature is allowed to increase to about 20°, rearrangement and substitution begin to occur.

These side reactions need not be detrimental in the case that the solvent is water, since rearrangement and substitution produce a 1,1-dihalo-3-hydroxy-4-methyl-1-pentene, which can be dehydrated to the desired 1,1-dihalo-4-methyl-1,3-pentadiene by known methods. To produce an optimum yield of a 1,1-dihalo-3-hydroxy-4-methyl-1-pentene, it is preferable that the base be a powdered alkali metal hydroxide, such as sodium, potassium, or lithium hydroxide, in at least a 2:1 molar ratio with respect to the tetrahalopentane. However, six to tenfold excess base may be employed if desired. Generally, the reaction mixture is heterogeneous, the tetrahalopentane comprising between about two and twenty percent by weight, so that vigorous strirring is desirable. Although some of the substitution product results at lower temperatures, the yield is improved if the reaction is conducted between about 60° and 110°. This reaction is further illustrated in Example III.

When the solvent is an alcohol, rearrangement followed by substitution are wasteful side reactions, since an ether results. It has been discovered that at about 0°, however, a mixture of a 1,1,1-trihalo-4-methyl-2-pentene and a 1,1,1-trihalo-4-methyl-3-pentene is produced in good yield. Surprisingly, simply heating this mixture at a temperature in the range of about 125°–175°, preferably about 150°, converts both olefins to a 1,1,3-trihalo-4-methyl-1-pentene, which then may be dehydrohalogenated to the desired 1,1-dihalo-4-methyl-1,3-pentadiene in a solvent of low nucleophilicity as described above, except that only one equivalent of base per mole of trihalopentene is required. These reactions will be clarified by reference to Example IV.

EXAMPLE II

Dehydrohalogenation of 1,1,1,3-Tetrahalo-4-methylpentaines Directly to 1,1-Dihalo-4-methyl-1,3-pentadienes a. 1,1-Dichloro-4-methyl-1,3-pentadiene from 1,1,1,3-Tetrachloro-4-methylpentane
   1. In n-heptane A stirred mixture of 100 grams (0.446 mole) of 1,1,1,3-tetrachloro-4-methylpentane and 100 grams (1.78 moles) of powdered potassium hydroxide in 1 liter of n-heptane was heated under reflux for 3 hours. Then an additional 100 grams (1.78 moles) of powdered potassium hydroxide was added to the reaction mixture, which was heated under reflux for an additonal 4 hours, after which another 50 gram portion (0.89 mole) of powdered potassium hydroxide was added, and refluxing was continued for one more hour. The reaction mixture was then allowed to cool to room temperature.

The reaction mixture was filtered with an admixed filter aid, and the filter cake was washed wih n-heptane, then wih methylene chloride. The methylene chloride was removed from the combined filtrates under reduced pressure; then the n-heptane was removed by distillation at atmospheric pressure. Lastly, the residue was distilled to give 22.7 grams (35% yield) of 1,1-dichloro-4-methyl-1,3-pentadiene; bp, 60°–70°/760 mm.

The following nmr analysis of the distillate is consistent with the assigned structure:

nmr $\delta$ ppm (CDCl$_3$): 1.07 (d,6H), 2.70–2.00 (m,1H), 6.17(d1H).

2. In toluene

A mixture of 5.0 grams (0.022 mole) of 1,1,1,3-tetrachloro-4-methylpentane and 10.0 grams (0.179 mole) of powdered potassium hydroxide in 100 ml of toluene was heated at 100° for 8 hours, at the end of which time gas chromatographic analysis of the reaction mixture indicated it to contain 78% 1,1-dichloro-4-methyl-1,3-pentadiene.

3. In xylene

A mixture of 5.0 grams (0.022 mole) of 1,1,1,3-tetrachloro-4-methylpentane and 10.0 grams (0.179 mole) of powdered potassium hydroxide in 100 ml of p-xylene was heated at 128° for 1 hour, at the completion of which gas chromatographic analysis of the reaction mixture indicated it to contain 82% 1,1-dichloro-4-methyl-1,3-pentadiene.

B. 1,1-Dichloro-4-methyl-1,3-pentadiene from 3-Bromo-1,1,1-trichloro-4-methylpentane
   1. In benzene 7.0 Grams (0.10 mole) of powdered potassium hydroxide was suspended in 100 ml of benzene in a reaction flask. The mixture was heated under reflux with a Dean-Stark trap for 20 minutes to remove moisture. Then 4.5 grams (0.015 mole) of 3-bromo-1,1,1-trichloro-4-methylpentane was added, and the reaction mixture was heated under reflux for 18 hours. After cooling the reaction mixture, it was filtered. The benzene was removed from the filtrate by evaporation under reduced pressure. Gas chromatographic analysis of the residue (4.7 grams) indicated it to contain 40% 1,1-dichloro-4-methyl-1,3-pentadiene.

2. In dioxane 7.0 Grams (0.10 mole) of powdered potassium hydroxide contained in a reaction flask was mixed with 100 ml of p-dioxane. To this mixture was added 4.5 grams (0.015 mole) of 3-bromo-1,1,1-trichloro-4-methylpentane. The reaction mixture was heated under reflux (101°) for 18 hours, then poured into water, and the aqueous mixture was extracted with methylene chloride. The organic phase was separated, washed with water, dried, then filtered. The solvent was removed under reduced pressure. Gas chromatographic analysis of the residue (1.7 grams) indicated it to contain 60% 1,1-dichloro-4-methyl-1,3-pentadiene.

EXAMPLE III

Synthesis of 1,1-Dichloro-3-hydroxy-4-methyl-1-pentene

A mixture of 20 grams (0.87 mole) of 1,1,1,3-tetrachloro-4-methylpentane and 40 grams (0.71 mole) of potassium hydroxide in 600 ml of water was heated under reflux (100°) for 3 hours. The reaction mixture was cooled and extracted with n-hexane. The extract was dried and filtered. The filtrate was evaporated to dryness to give 12.1 grams of residue, which was distilled, yielding 6.17 grams (54% yield) 1,1-dichloro-3-hydroxy-4-methyl-1-pentene; bp, 90°–115°/25–27mm.

Analysis: nmr $\delta$ ppm (CDCl$_3$): 0.95(d,6H), 2.12–1.48(m,1H), 2.81 (s,1H), 4.18(dd,1H), 5.90(d,1H).

ir (liq., cm$^{-1}$): 3300, 1615, 1385, 1365.

EXAMPLE IV

Stepwise Dehydrohalogenation of 1,1,1,3-Tetrahalo-4-methylpentanes to 1,1-Dihalo-4-methyl-1,3-pentadienes A. Synthesis of a Mixture of a 1,1,1-Trihalo-4-methyl-2-pentene and a 1,1,1-Trihalo-4-methyl-3-pentene 1. Synthesis of a mixture of 1,1,1-trichloro-4-methyl-2-pentene and 1,1,1-trichloro-4-methyl-3-pentene from 1,1,1,3-tetrachloro-4-methylpentane A solution of 26.2 grams (0.4 mole) of potassium hydroxide in 200 ml of ethanol was cooled to 4°, and 50 grams (0.21 mole) of 1,1,1,3-tetrachloro-4-methylpentane was added. The reaction mixture was stirred at 3° for 5 hours, refrigerated at about 0° for 16 hours, and then stirred an additional 2 hours at 0°. Potassium chloride was filtered from the reaction mixture. To the filtrate was added 500 ml of water. The aqueous mixture was extracted with four-200 ml portions of methylene chloride. The combined extracts were washed with four-100 ml portions of water, then dried over magnesium sulfate. The mixture was filtered; ethanol and water were removed by evaporation to give 42.7 grams of an oil, which gas chromatographic analysis indicated comprised 45.2% 1,1,1-trichloro-4-methyl-2-pentene and 44.8% 1,1,1-trichloro-4-methyl-3-pentene. The mixture was distilled without fractionation, giving 34.4 grams (87% yield) of a mixture of 1,1,1-trichloro-4-methyl-2-pentene and 1,1,1-trichloro-4-methyl-3-pentene; bp, 80°–110°/30 mm.

Analysis: Calc'd for $C_6H_9Cl_3$: C,38.4; H,4.8; Found: C,37.9; H,4.9.

Mass spec: Single component, m/e 187.5.

2. Synthesis of a mixture of 1,1,1-trichloro-4-methyl-2-pentene and 1,1,1-trichloro-4-methyl-3-pentene from 3-bromo-1,1,1-trichloro-4-methylpentane A solution of 6.6 grams (0.1 mole) of potassium hydroxide in 25 ml of ethanol was cooled to 0°, and 21.1 grams (0.09 mole) of 3-bromo-1,1,1-trichloro-4-methylpentane was added. The reaction mixture stood at 0° for 48 hours. Then 150 ml of methylene chloride was added to the reaction mixture, and potassium bromide was removed by filtration. The filtrate was washed with water and dried with magnesium sulfate. The filtrate was concentrated under reduced pressures to 20 grams of yellow oil. Gas chromatographic analysis of the oil indicated that it contained 58.50% 1,1,1-trichloro-4-methyl-2-pentene and 8.11% 1,1,1-trichloro-4-methyl-31-pentene.

B. Synthesis of 1,1,3-Trichloro-4-methyl-1-pentene from a Mixture of 1,1,1-Trichloro-4-methyl-2-pentene and 1,1,1-Trichloro-4-methyl-3-pentene 5.0 Grams of a mixture of 1,1,1-trichloro-4-methyl-2-pentene and 1,1,1-trichloro-4-methyl-3-pentene, prepared as described in Example IV A.1., was heated in a pressure bottle at 150° for 5 hours. Gas chromatographic analysis of the mixture indicated an 82.5% conversion to 1,1,3-trichloro-4-methyl-1-pentene.

Analysis: nmr δ ppm $(CDCl_3)$ 1.01(d,6H), 2.28–1.70(m1H), 4.52(q,1H), 6.05(d,1H).

C. Synthesis of 1,1-Dichloro-4-methyl-1,3-penadiene from 1,1,3-Trichloro-4-methyl-11-pentene A mixture of 30 grams (0.160 mole) of 1,1,3-trichloro-4-methyl-1-pentene and 30 grams (0.53 mole) of powdered potassium hydroxide in 500 ml of n-heptane in a Morton flask was stirred under reflux (98°) for 10 hours. An additional 30 grams (0.53 mole) of powdered potassium hydroxide was then added and the heating and stirring were resumed for 4 hours.

The reaction mixture was cooled, and approximately 500 ml of water was added. The organic layer was separated and dried. The dried solution was filtered and the n-heptane was removed by distillation. The residue was distilled under vacuum to give 1,1-dichloro-4-methyl-1,3-pentadiene; bp, 95°–100°/25 mm.

I claim:

1. A process for producing 1,1-dichloro-4-methyl-1,3-penadiene which comprises
   a. condensing a carbon tetrahalide, selected from the group consisting of carbon tetrachloride, bromotrichloromethane, and dibromodichloromethane, with 3-methyl-11-butene in the presence of a free radical catalyst to produce a 1,1,1,3-tetrahalo-4-methylpentane; and then
   b. treating the 1,1,1,3-tetrahalo-4-methylpentane with an alkali metal hydroxide at a temperature between about 100° C and 150° C in a solvent selected from the group consisting of hydrocarbons and ethers, causing dehydrohalogenation, eliminating two moles of hydrohalic acid, producing said 1,1-dichloro-4-methyl-1,3-pentadiene.

2. The process of claim 1 wherein the carbon tetrahalide is carbon tetrachloride.

3. The process of claim 1 wherein the carbon tetrahalide is bromotrichloromethane.

4. A process for producing 1,1-dichloro-4-methyl-1,3-pentadiene which comprises
   a. condensing a carbon tetrahalide, selected from the group consisting of carbon tetrachloride, bromotrichloromethane, and dibromodichloromethane, with 3-methyl-11-butene in the presence of a free radical catalyst to produce a 1,1,1,3-tetrahalo-4-methylpentane; and then
   b. treating the 1,1,1,3-tetrahalo-4-methylpentane with an alkali metal hydroxide at a temperature of about 0° C in a solvent selected from the group consisting of alcohols and water, causing dehydrohalogenation, eliminating one mole of hydrohalic acid, producing a mixture of a 1,1,1-trihalo-4-methyl-2-pentene and a 1,1,1-trihalo-4-methyl-3-pentene; and then
   c. heating the mixture of pentenes at a temperature between about 125° C and 175° C, causing isomerization, yielding a 1,1,3-trihalo-4-methyl-1-pentene; and then
   d. treating the 1,1,3-trihalo-4-methyl-1-pentene with an alkali metal hydroxide at a temperature between about 100° C and 150° C in a solvent selected from the group consisting of hydrocarbons and ethers, causing dehydrohalogenation, eliminating a second mole of hydrohalic acid, producing 1,1-dichloro-4-methyl-1,3-pentadiene.

5. The process of claim 4 wherein the 1,1,1,3-tetrahalo-4-methylpentane is 1,1,1,3-tetrachloro-4-methylpentane.

6. The process of claim 4 wherein the 1,1,1,3-tetrahalo-4-methylpentane is 3-bromo-1,1,1-trichloro-4-methylpentane.

7. A process for producing 1,1-dichloro-4-methyl-1,3-pentadiene which comprises treating a 1,1,1,3-tetrahalo-4-methylpentane, selected from the group consisting of 1,1,1,3-tetrachloro-4-methylpentane, 3-bromo-1,1,1-trichloro-4-methylpentane and 1,3-dibromo-1,1-dichloro-4-methylpentane, with an alkali metal hydroxide at a temperature between about 100° C and 150° C in a solvent selected from the group consisting of hydrocarbons and ethers, causing dehydrohalogenation, eliminating two moles of hydrohalic acid, producing said 1,1-dichloro-4-methyl-1,3-pentadiene.

8. The process of claim 7 wherein the 1,1,1,3-tetrahalo-4-methylpentane is 1,1,1,3-tetrachloro-4-methylpentane.

9. The process of claim 7 wherein the 1,1,1,3-tetrahalo-4-methylpentane is 3-bromo-1,1,1-trichloro-4-methylpentane.

10. A process for producing 1,1-dichloro-4-methyl-1,3-pentadiene which comprises
    a. treating a 1,1,1,3-tetrahalo-4-methylpentane, selected from the group consisting of 1,1,1,3-tetrachloro-4-methylpentane, 3-bromo-1,1,1-trichloro-4-methylpentane and 1,3-dibromo-1,1-dichloro-4-methylpentane, with an alkali metal hydroxide at a temperature of about 0° C in a solvent selected from the group consisting of alcohols and and water, causing dehydrohalogenation, eliminating one mole of hydrohalic acid, producing a mixture of a 1,1,1-trihalo-4-methyl-2-pentene and a 1,1,1-trihalo-4-methyl-3-pentene; and then b. heating the mixture of pentenes at a temperature between about 125° C nd 175° C, causing isomerization, yielding a 1,1,3-trihalo-4-methyl-1l -pentene; and then c. treating the 1,1,3-trihalo-4-methyl- 1-pentene with an alkali metal hydroxide at a temperature between about 100° C and 150° C in a solvent selected from the group consisting of hydrocarbons and ethers, causing dehydrohalogenation, eliminating a second mole of hydrohalic acid, producing 1,1-dichloro-4-methyl-1,3-pentadiene.

11. The process of claim 10 wherein the 1,1,1,3-tetrahalo-4-methylpentane is 1,1,1,3-tetrachloro-4-methylpentane.

12. The process of claim 10 wherein the 1,1,1,3-tetrahalo-4-methylpentane is 3-bromo-1,1,1-trichloro-4-methylpentane.

* * * * *

UNITED STATES PATENT AND TRADEMARK OFFICE
CERTIFICATE OF CORRECTION

PATENT NO. : 4,070,404
DATED : January 24, 1978
INVENTOR(S) : Andrew Lupichuk

It is certified that error appears in the above-identified patent and that said Letters Patent are hereby corrected as shown below:

Col. 3, line 40, "the" should read --The--.
Col. 5, line 16, "a" should read --at--.
Col. 7, line 26, "methylpentaines" should read --methylpentanes--.
line 29, "a." should read --A.--.
line 45, "wih" should read --with--.
Col. 8, line 57, a period and paragraph should occur after methylpentane.
Col. 9, line 27, "methy-31" should read --methyl-3- --.
line 28, "-pentene" should read --pentene--.
line 40, "penadiene" should read --pentadiene--.
line 41, "4-methyl-11-pentene" should read --4-methyl-1-pentene--.
line 57, "penadiene" should read --pentadiene--.
line 61, "3-methyl-11-butene" should read --3-methyl-1-butene--.
Col.10, line 12, "3-methyl-11-butene" should read --3-methyl-1-butene--.
Col.11, line 4, "nd" should read --and--.
line 5, "1,1,3-trihalo-4-methyl-1]-pentene" should read
--1,1,3-trihalo-4-methyl-1-pentene--.

Signed and Sealed this

Eleventh Day of July 1978

[SEAL]

Attest:

RUTH C. MASON
*Attesting Officer*

DONALD W. BANNER
*Commissioner of Patents and Trademarks*